US007139363B2

(12) United States Patent
Misawa et al.

(10) Patent No.: US 7,139,363 B2

(45) Date of Patent: Nov. 21, 2006

(54) OBLIQUE-VIEW CONE-BEAM CT SYSTEM

(75) Inventors: Masaki Misawa, Tsukuba (JP); Ion Tiseanu, Bucharest (RO)

(73) Assignee: National Institute of Advanced Industrial Science and Technology, Tokyo (JP)

( * ) Notice: Subject to any disclaimer, the term of this patent is extended or adjusted under 35 U.S.C. 154(b) by 0 days.

(21) Appl. No.: 10/379,702

(22) Filed: Mar. 6, 2003

(65) Prior Publication Data

US 2004/0017882 A1 Jan. 29, 2004

(30) Foreign Application Priority Data

Mar. 6, 2002 (JP) ............................ 2002-061071

(51) Int. Cl.
*G01N 23/00* (2006.01)

(52) U.S. Cl. ............................... 378/11; 378/4; 378/20

(58) Field of Classification Search ............... 378/4–23
See application file for complete search history.

(56) References Cited

U.S. PATENT DOCUMENTS 5,463,667 A 10/1995 Ichinose et al.
5,740,224 A * 4/1998 Muller et al. ................. 378/11
5,995,581 A * 11/1999 Ozaki .......................... 378/20
6,459,759 B1 10/2002 Tominaga

FOREIGN PATENT DOCUMENTS

| | | |
|---|---|---|
| JP | 63157046 | 6/1988 |
| JP | 2000-329710 | 11/2000 |
| JP | 2001-153817 | 6/2001 |
| WO | WO 01/61326 | 8/2001 |

OTHER PUBLICATIONS

Takami Kai et al. "Application of Fast X-ray CT Scanner to Visualization of Bubbles in Fluidized Bed", Journal of Chemical Engineering of Japan, vol. 33 (2000), No. 6. pp. 906-909.

* cited by examiner

*Primary Examiner*—Edward J. Glick
*Assistant Examiner*—Jurie Yun
(74) *Attorney, Agent, or Firm*—Sughrue Mion, PLLC

(57) ABSTRACT

An oblique-view cone-beam CT system comprising an X-ray source for irradiating an object with X-ray from an oblique direction with respect to a rotational axis of said object. A detector is provided for detecting projection images resulting from the X-ray irradiation. A computer electrically connected to the detector is provided for recording the detected projection images and reconstructing the recorded projection images to provide a 3-dimensional image.

3 Claims, 7 Drawing Sheets

OBLIQUE-VIEW CONE-BEAM CT SYSTEM

FIELD

This disclosure teaches techniques related to oblique-view cone-beam computed tomography (CT). Devices using these techniques are usable in several applications including, but not limited to, industrial X-ray CT systems, nondestructive inspection systems for semiconductor components, printed boards, IC chips, mechanical components, composite materials or plastic materials, or medical CT systems for hard tissues such as bone or teeth.

BACKGROUND

In a conventional 3-dimensional X-ray or cone-beam CT system, an X-ray source A, a sample D and a 2-dimensional detector B are disposed in one plane as shown in FIG. 5. The sample D is irradiated with X-ray from a direction perpendicular to (at 90 degrees with) a rotational axis C of the sample D. The projected image is received by the 2-dimensional detector B.

In such a cone-beam CT system, the X-ray generator or source cannot be moved sufficiently close to the rotating object due to its large rotation radius. Thus, even if one attempts to acquire a magnified image of a part of an object having a large surface area, a desired magnification cannot be obtained. In addition, when projection data on an object having a large flat surface area are acquired by irradiating the object with X-ray from a direction perpendicular to a rotational axis of the sample, beam hardening is undesirably generated in a direction parallel to the flat surface.

Beam hardening is described asunder. When X-rays having a sequence of spectrum penetrates through an object, low energy constituents appear to be attenuated more than their actual attenuation. This is believed to be because it is greater than the attenuation of high energy constituents. Because of this, when an image reconstruction calculation is performed where an effect of the spectrum is not considered, even a uniform substance appear non uniform. This effect is called beam hardening.

Japanese Patent Laid-Open Publication No. 2001-153817 discloses a laminography technique where an object is imaged from an oblique direction with respect to a rotational axis of the object. In such a laminography technique, several sets of 2-dimensional image data are generated. These 2-dimensional image data sets are then superimposed together 3dimensionally. Such a laminography technique enables one to make desirable observations in the 2-dimensional plane. However a clear 3-dimensional image can not be obtained due to insufficient resolution in height direction.

The disclosed teachings is aimed at overcoming some of the disadvantages in the conventional cone beam CT systems.

SUMMARY

To realize the advantages of the disclosed teachings there is provided an oblique-view cone-beam CT system comprising an X-ray source for irradiating an object with X-ray from an oblique direction with respect to a rotational axis of said object. A detector is provided for detecting projection images resulting from the X-ray irradiation. A computer electrically connected to the detector is provided for recording the detected projection images and reconstructing the recorded projection images to provide a 3-dimensional image.

More specifically, the CT system further includes a rotatable table for placing said object thereon.

In another specific enhancement the CT system further includes a swingable and vertically movable tilting frame for mounting said X-ray source and said detector thereon.

More specifically, the CT system further includes a swingable and vertically movable tilting frame for mounting said X-ray source and said detector thereon while interposing therebetween said object placed on said rotatable table.

Another aspect of the disclosed teachings is a method of obtaining images of a sample using an oblique-view cone-beam CT system comprising acquiring projection images by positioning a detector to allow a normal line passing through a detection-surface center of the detector to be oriented to a focal point of an X-ray source. The projection images are converted such that the normal line becomes perpendicular to the rotational axis of the sample. The converted projection images are multiplied by a weighting factor depending on the distance between the X-ray and the rotational axis of the sample and image coordinates Y, Z to produce weighted projection data. The weighted projection data is fourier-transformed with respect to the Y coordinate. A convolution is performed by processing by a filter function in a frequency domain The Fourier-transformed data is back projected onto a 3-dimensional reconstruction grid.

BRIEF DESCRIPTION OF THE DRAWINGS

The above objectives and advantages of the disclosed teachings will become more apparent by describing in detail preferred embodiment thereof with reference to the attached drawings in which.

DETAILED DESCRIPTION

With reference to the drawings, a system embodying the disclosed teachings is described herein.

Figure 1:
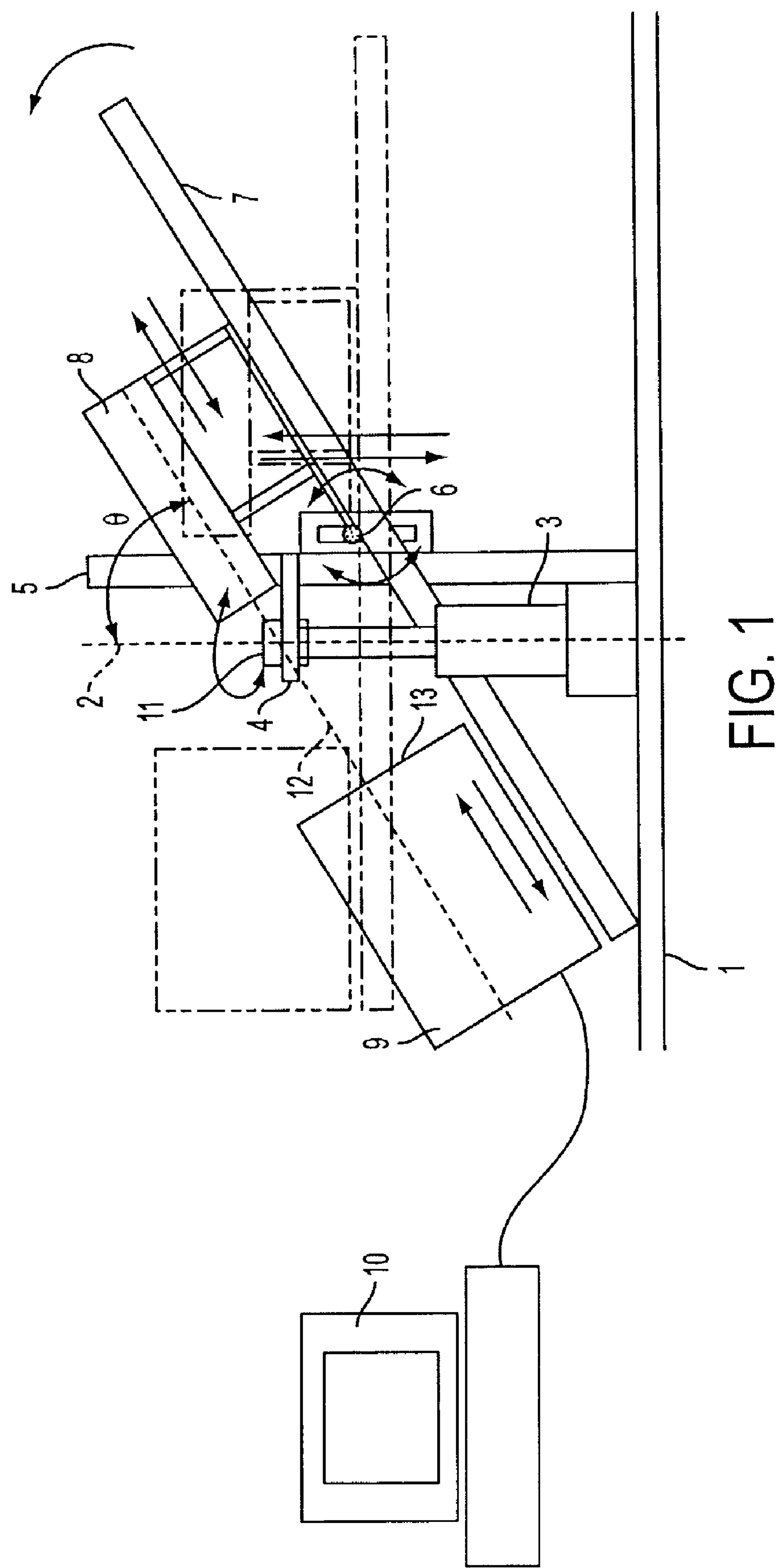
FIG. 1 is a front view of an oblique-view cone-beam CT system according to one embodiment of the present invention.

FIG. 1 is a front view of an example of an oblique-view cone-beam CT system embodying the disclosed teachings. A sample-mounting table 3, driven by a driving device (not shown), is rotatably mounted on a rotary stage 1. The table 3 is coaxial to a rotational axis 2 of the rotary stage 1. A sample 4 which is an object to be inspected and measured is placed on the sample-mounting table 3.

A supporting column 5 is located adjacent to the rotary stage 1. A tilting frame 7 is attached to the supporting column 5 in such manner that it is swingable about a horizontal support shaft 6 provided in the supporting column 5. The axis of rotation of this swinging action is clear from FIG. 1, as indicated by the hatched lines depicting the position of the tilting frame when it is horizontal. In addition, this horizontal support shaft 6 is supported by the supporting column 5 in such manner that it is vertically movable along the supporting column 5. An X-ray source 8 and a detector 9 are mounted, respectively, at one end and the other end of the tilting frame 7 while interposing the sample 4 therebetween. Each of the X-ray source 8 and the detector 9 is mounted on the tilting frame in such manner that it can be moved close to and away from the sample 4.

Thus, the sample 4 can be adequately irradiated with X-ray from the X-ray source 8 by swinging the tilting frame 7 to adjust an irradiation angle of the X-ray source 8 and moving the X-ray source 8 close to or away from the sample 4. Depending on the configuration of the sample 4 and/or the position of a target region of the sample 4 to be detected and observed with magnification, the position, angle and the closeness of the X-Ray source 8 to the sample 4 can be is adjusted.

The reference numeral 10 is a data recording/analyzing personal computer which is electrically connected to the detector 9.

An example operation of detecting projection images is described herein. In this example a target region 11 which is the central region of the sample 4 having a large flat surface area and a thin thickness is to be imaged. The sample 4 is placed on the rotary stage 1. The irradiation direction of the X-ray 12 from the X-ray source 8 is oriented to the target region 11. This is done by swinging the tilting frame 7 counterclockwise the desired anble and fixing its position at a desired closeness to the target area as shown in FIG. 1. The X-ray is then transmitted through the sample.

At this position, the direction of X-ray 12 and the rotational axis 2 of the rotary stage 1 intersect at an angle θ which is less than 90 degrees.

Then, the rotary stage 1 is rotated about the rotatable axis 2 at small-angular intervals while irradiating the sample 4 with X-ray 12 from the X-ray source 8. The sample-mounting table 3 is simultaneously rotated. Thus, projection images at respective angles are projected onto and detected by the detector 9. The projected images detected by the detector 9 are transferred to and recorded by the data recording/analyzing personal computer 10.

The respective angle of the X-ray source 8 and the detector 9 and the irradiation direction of the X-ray 12 can be freely set by swinging the tilting frame 7 about the horizontal support shaft 6. The distance is adjusted by vertically moving the horizontal support shaft 6 along the supporting column 5.

The following steps describe how a 3-dimensional image of the target region 11 of the sample 4 is created using the projection images created by the disclosed system and recorded in the data recording/analyzing personal computer 10.

(Step 1) Projection images acquired by positioning the detector 9 to allow a normal line passing through the detection-surface center 13 of the detector 9 to be oriented to a focal point of the X-ray source 8 are converted such that the normal line to the detection-surface center 13 becomes perpendicular to the rotational axis 2 of the sample 4.

Figure 7:
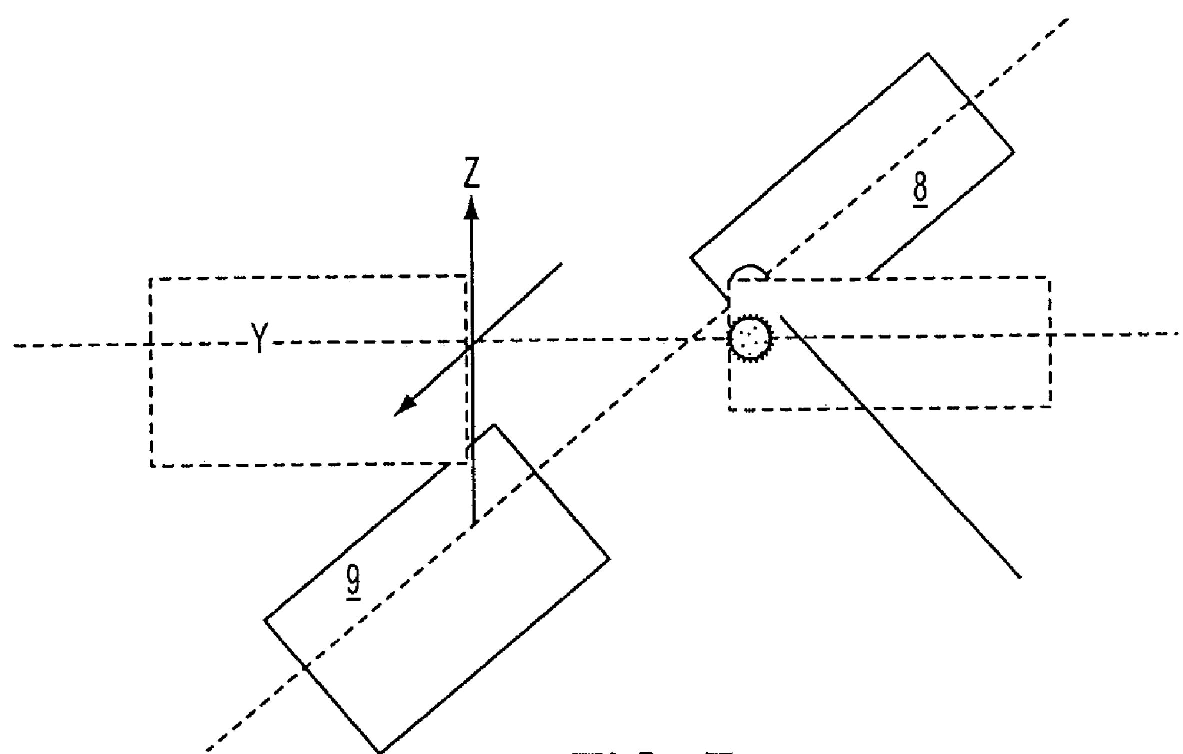
FIG. 7 shows the Y and Z coordinates and the focal point.

(Step 2) The converted projection image data are multiplied by a weighting factor consisting of the distance between the X-ray 12 and the rotational axis 2 of the sample 4, and image coordinates Y, Z, to produce weighted projection data. In this step, a coordinate system having its origin in a horizontal plane including the focal point of the X-ray source 8 are used to determine the Y and Z coordinate values. FIG. 7 shows the Y and Z coordinates and the focal point.

(Step 3) The weighted projection data are Fourier-transformed with respect to the Y coordinate and processed by a filter function in a frequency domain to perform the convolution.

(Step 4) The Fourier-transformed data are back-projected onto a 3-dimensional reconstruction grid.

The following equations are an example explaining the above steps:

$$f(t,s,z)=\frac{1}{2}\int_0^{2\pi}\frac{D_{SO}^2}{(D_{so}-s)^2}\int_{-\infty}^{\infty}P_\beta(Y,Z)h\left(\frac{D_{SO}t}{D_{SO}-s}-Y\right)\frac{D_{so}}{\sqrt{D_{SO}^2+Y^2+Z^2}}\,d\beta dY$$

where $$t=x\cos\beta+y\sin\beta$$

$$s=-x\sin\beta+y\cos\beta$$

The weighting factor is given by $D_{SO}/\sqrt{D^2_{SO}+Y^2+Z^2}$. As noted above Y and Z are based on a coordinate system that has its origin in a horizontal plane that also contains the focal point of the X-ray source. $P_\beta(Y,Z)$ represents the converted image data. $D_{so}$ is the distance between focal point of X-ray source and the sample center. The distance between $D_{so}$ and the detection surface is represented by s. The resulting distribution of absorption coefficient is denoted by f(t,s,z).

The magnification of a part of the sample 4 can be freely adjusted by changing the distance between the X-ray source 8 and the sample 4 on the tilting frame 7 while maintaining the tilt angle θ of the tilting frame 7, which is defined by the X-ray 12 and the rotational axis 2, at a certain value.

The tilt angle θ of the tilting frame 7 can be changed to select the X-ray irradiation direction with respect to the target region 11 of the sample 4, so as to prevent X-ray attenuation from being excessively reduced.

A conventional 3-dimensional CT image can also be obtained by positioning the tilting frame 7 in a horizontal position.

The arrangement of the sample 4, the X-ray source 8 and the detector 9 as shown in FIG. 1 makes it possible to eliminate the need for transmitting the X-ray in the direction parallel to the flat surface of the sample 4, so that the transmission distance of X-ray is reduced, and an adverse affect from beam hardening is significantly suppressed to provide an improved image having enhanced contrast. In addition, lower-energy X-ray can be used to increase the life of the X-ray source 8.

Figure 2:
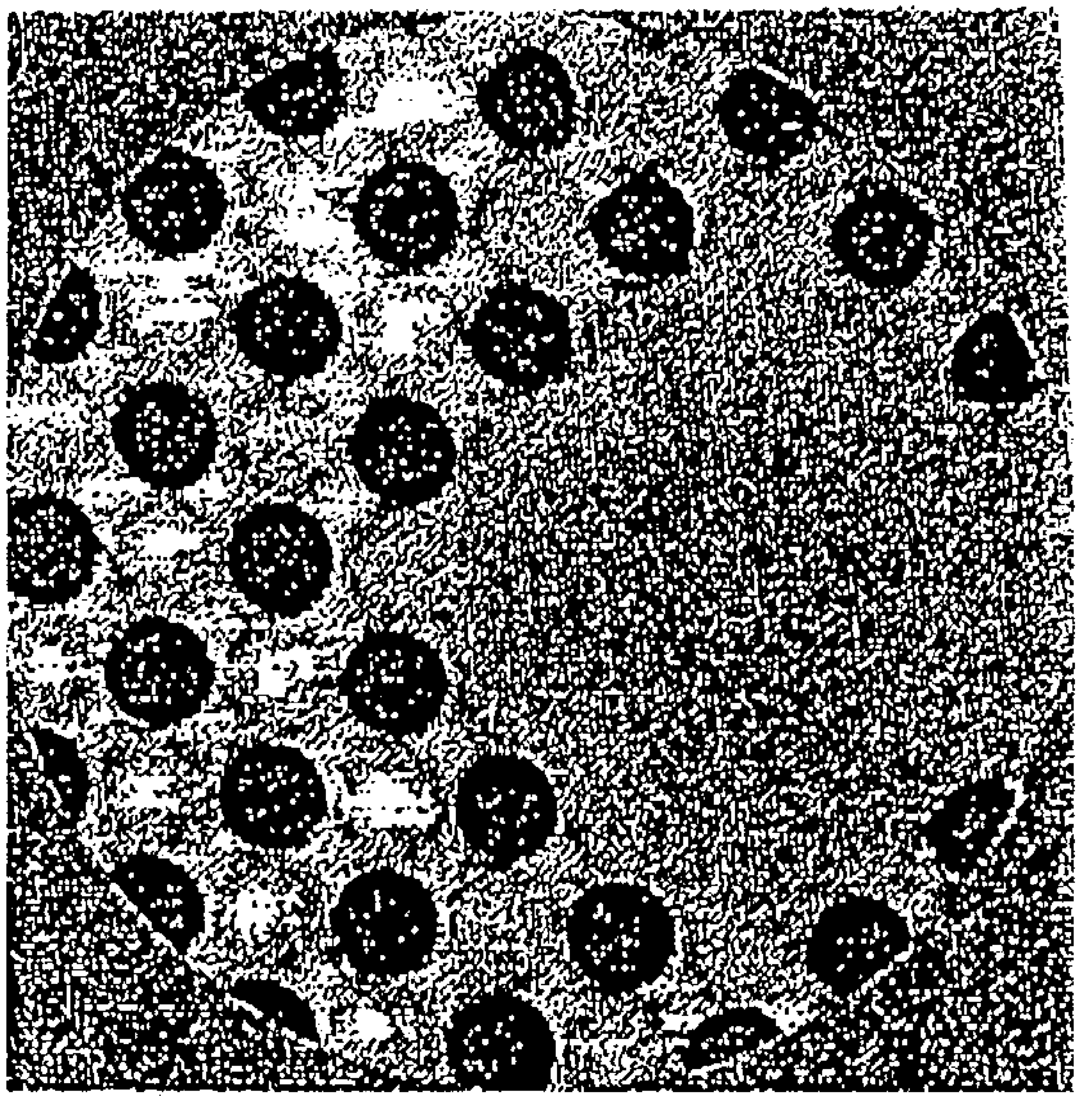
FIG. 2 is a top plan view showing an example of a 3-dimensionally visualized image obtained by imaging a part of a ball-grid-array chip under magnification radiography at an oblique angle of 25 degree.
Figure 3:
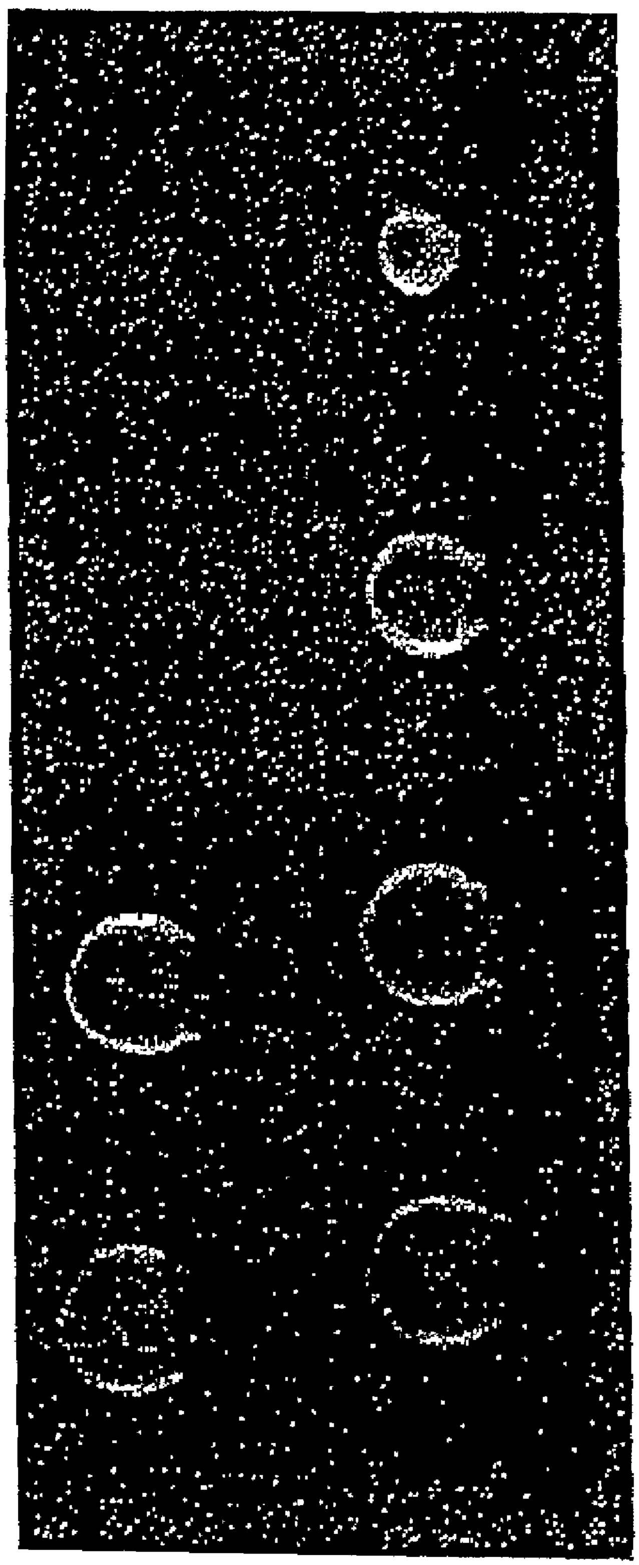
FIG. 3 is a side view showing the 3-dimensionally visualized image in FIG. 2.

FIGS. 2 and 3 show an example of a 3-dimensionally visualized image obtained by imaging a part of a ball-grid-array (BGA) chip under magnification radiography at a tilt or oblique angle of 25 degree. FIG. 2 is a top plan view of the central region of the BGA chip, and FIG. 3 is a side view of the BGA chip.

As seen from these figures, each configuration of balls of the BGA chip is clearly visualized.

Figure 4:
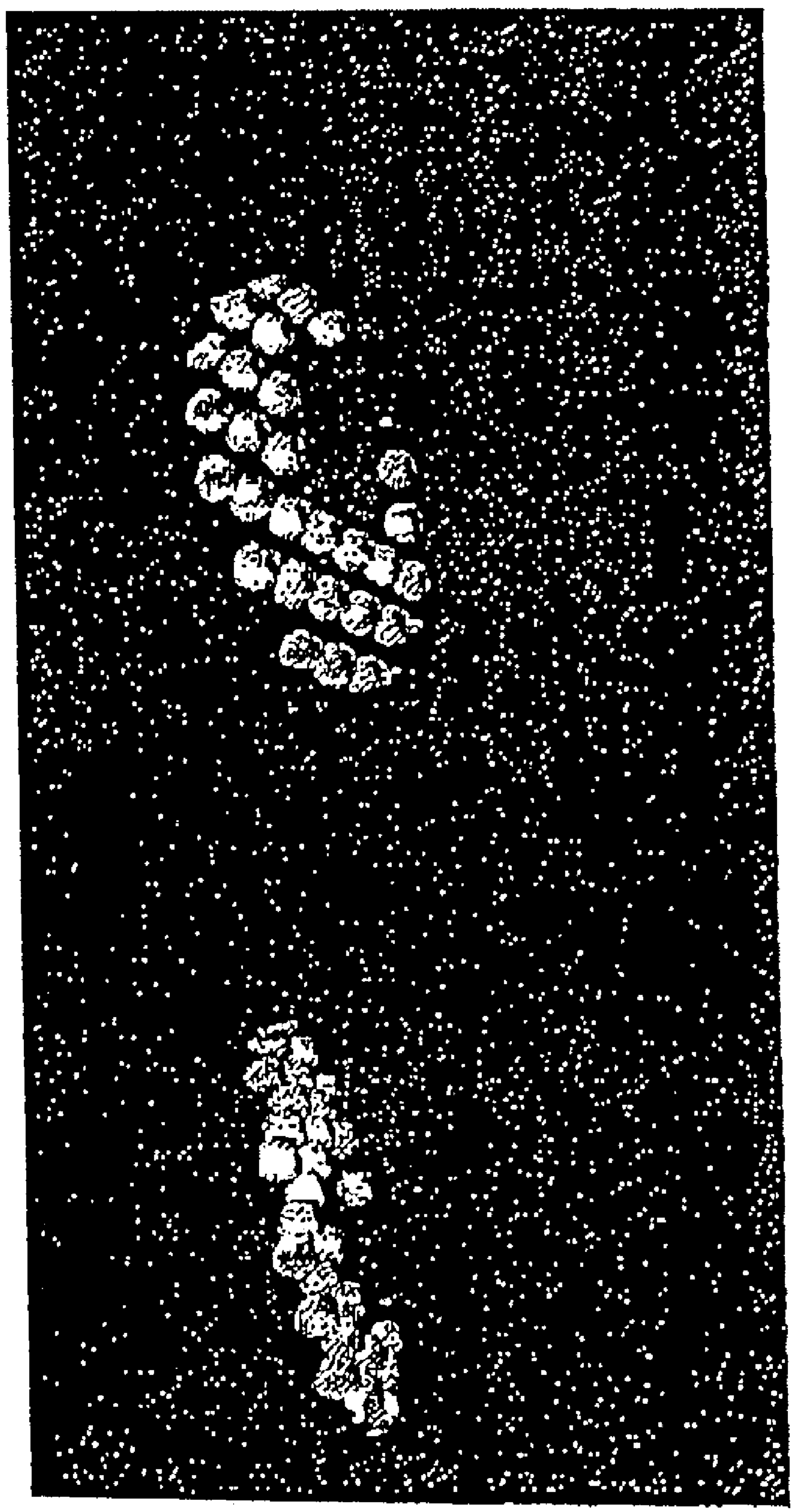
FIG. 4 shows an example of a 3-dimensionally visualized image of solder balls of a ball-grid-array chip.

FIG. 4 shows an example of a 3-dimensionally visualized image of solder balls of a BGA chip. It can be observed that the configuration of the lower portion of the ball fusedly attached onto a chip substrate is 3-dimensionally represented.

Figure 5:
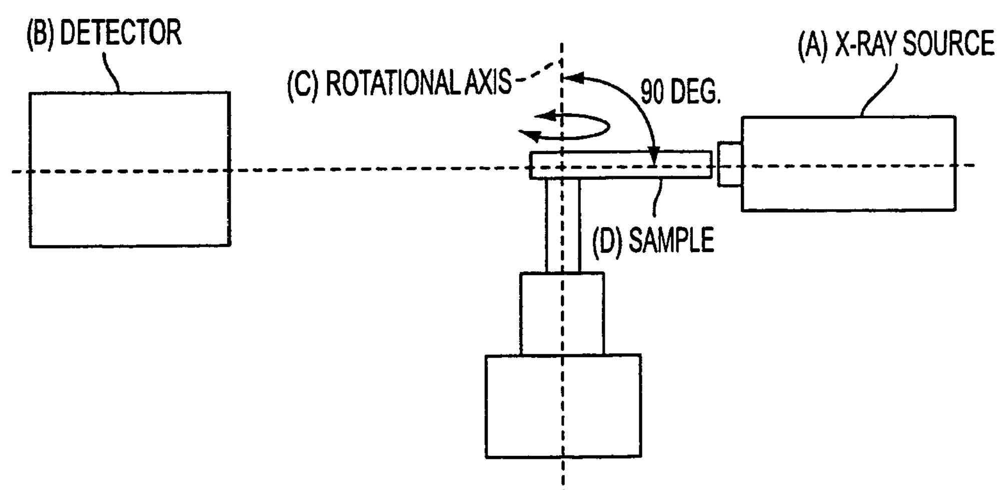
FIG. 5 is a front view of a conventional cone-beam CT system.
Figure 6:
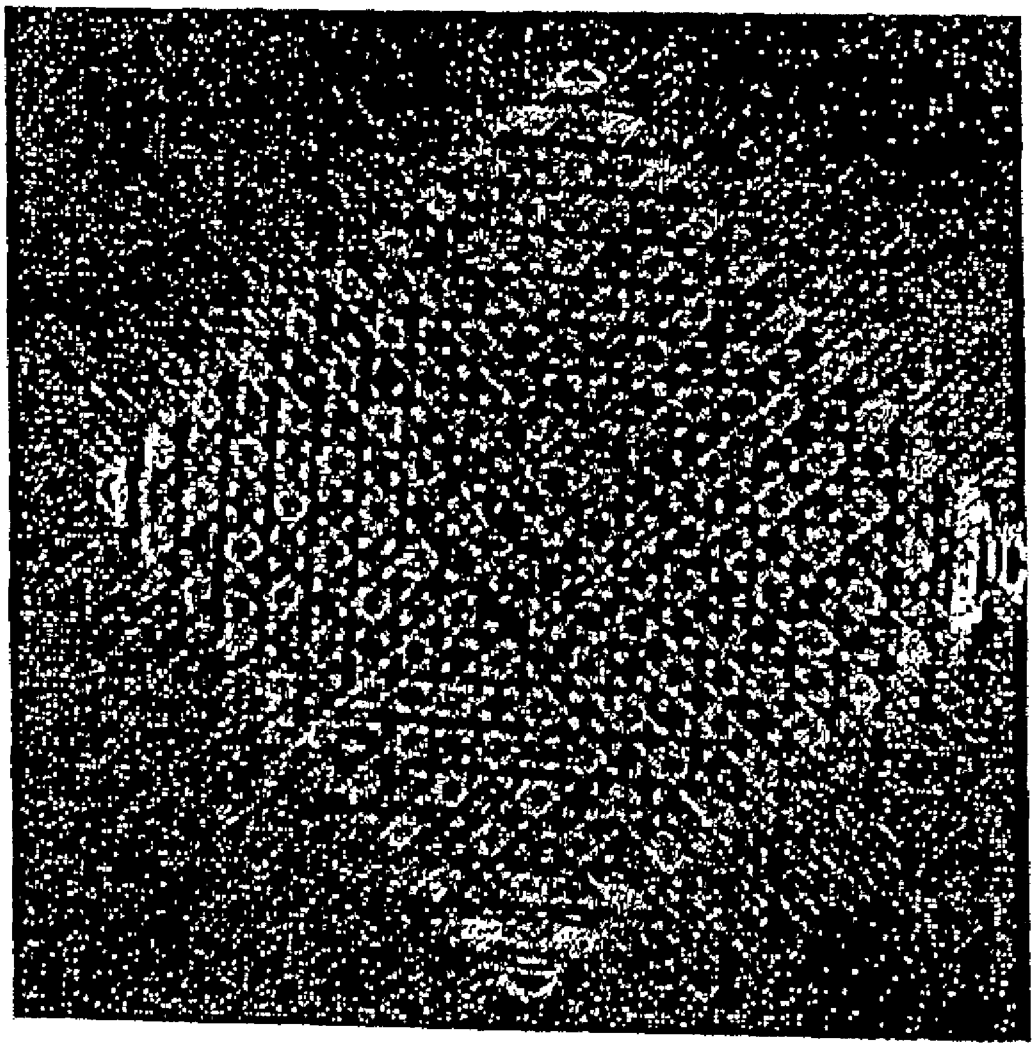
FIG. 6 shows a tomographic image of a ball-grid-array chip imaged by the conventional cone-beam CT system.

FIG. 6 shows a tomographic image of a BGA chip imaged by a conventional cone-beam CT system as shown in FIG. 5. In such a case, the tilting frame 7 is placed in a horizontal position. In the arrangement of the sample, the X-ray source and the detector are as shown in FIG. 5, the X-ray inevitably transmits through all of the solder balls located in one plane. This results in strong X-ray attenuation causing beam hardening. Consequently, despite there being no solder balls in the central region of the BGA chip, some solder balls are incorrectly observed as if they exist therein.

As mentioned above, in the oblique-view cone-beam CT system based on the disclosed teachings, the X-ray source is not disposed in the same plane as that of the object. Thus, even if the object has a large flat surface area, the X-ray source can be moved sufficiently close to the region of the object to be imaged with sufficient magnification while rotating the object, to obtain a 3-dimensional local image of the object.

The oblique-view cone-beam CT system of the present invention can also eliminate the need for transmitting X-ray in a direction parallel to the flat surface of the object. This makes it possible to reduce the transmission distance of X-ray and significantly suppress an adverse affect caused by beam hardening. This provides an improved image having enhanced contrast and clearness. Further, because lower-energy X-ray can be used, the life of the X-ray source is extended.

Other modifications and variations to the invention will be apparent to those skilled in the art from the foregoing disclosure and teachings. Thus, while only certain embodiments of the invention have been specifically described herein, it will be apparent that numerous modifications may be made thereto without departing from the spirit and scope of the invention.

What is claimed is:

1. An oblique-view cone-beam CT system comprising:

a rotating table to position an object, the rotating table operable to rotate the object around a rotational axis of the object;

an X-ray source for irradiating the object with central X-ray perpendicularly intersecting the detector surface from an oblique direction with respect to the rotational axis of said object, the system operable to tilt the X-ray source such that central beam is at a position of at least up to 90° from said rotational axis of the object;

a detector for detecting projection images resulting from the X-ray irradiation; and a computer electrically connected to the detector for recording the detected projection images and reconstructing the recorded projection images to provide a 3-dimensional reconstructed image.

2. The oblique-view cone-beam CT system as defined in claim 1, further including:

a swingable and vertically movable tilting frame for mounting said X-ray source and said detector thereon.

3. The oblique-view cone-beam CT system as defined in claim 1, further including:

a swingable and vertically movable tilting frame for mounting said X-ray source and said detector thereon while interposing there between said object placed on said rotatable table.

* * * * *